United States Patent [19]

Oberhardt et al.

[11] Patent Number: 5,350,676
[45] Date of Patent: Sep. 27, 1994

[54] METHOD FOR PERFORMING FIBRINOGEN ASSAYS USING DRY CHEMICAL REAGENTS CONTAINING MAGNETIC PARTICLES

[75] Inventors: Bruce J. Oberhardt, Raleigh; Nancy Gresalfi, Durham, both of N.C.

[73] Assignee: Cardiovascular Diagnostics, Inc., Durham, N.C.

[21] Appl. No.: 62,334

[22] Filed: May 17, 1993

Related U.S. Application Data

[63] Continuation of Ser. No. 550,570, Jul. 10, 1990, abandoned.

[51] Int. Cl.$^5$ .................. C12Q 1/00; C12Q 1/56; G01N 33/86; G01N 33/00
[52] U.S. Cl. .................. 435/13; 435/4; 422/73; 436/69; 73/64; 73/43; 356/39
[58] Field of Search .................. 435/4, 13, 805, 970; 422/73; 436/69; 73/64.43; 364/413.09; 356/39

[56] References Cited

U.S. PATENT DOCUMENTS

| | | | |
|---|---|---|---|
| 3,861,197 | 1/1975 | Adler | 436/69 |
| 4,756,884 | 7/1988 | Hillman et al. | 422/73 |
| 4,849,340 | 7/1989 | Oberhardt | 435/13 |
| 5,110,727 | 5/1992 | Oberhardt | 435/13 |
| 5,156,974 | 10/1992 | Grossmann | 436/69 |

FOREIGN PATENT DOCUMENTS 4798172 4/1974 Australia.

OTHER PUBLICATIONS

Oberhardt, B. J. et al. "Dry Reagent Technology for Rapid Convenient Measurements of Blood Coagulation and Fibrinology", *Clincal Chemistry*, vol. 37, No. 4, 1991.

*Primary Examiner*—Michael G. Wityshyn
*Assistant Examiner*—T. J. Reardon
*Attorney, Agent, or Firm*—Oblon, Spivak, McClelland, Maier & Neustadt

[57] ABSTRACT

An apparatus and a method for performing a fibrinogen assay are disclosed. The reaction slide bears a sample well for receiving a liquid sample and a reaction chamber in fluid communication with the sample well. The reaction chamber contains a dry reagent matrix in which is embedded a plurality of magnetic particles. A whole blood or blood-derived sample added to the sample well is introduced simultaneously into the reaction chamber where it solubilizes the reagent, freeing the magnetic particles and allowing them to move in an oscillating pattern. This oscillating pattern is optically monitored to measure the concentration of clottable fibrinogen in the sample.

19 Claims, 5 Drawing Sheets

METHOD FOR PERFORMING FIBRINOGEN ASSAYS USING DRY CHEMICAL REAGENTS CONTAINING MAGNETIC PARTICLES

This application is a continuation of application Ser. No. 07/550,570, filed on Jul. 10, 1990.

BACKGROUND OF THE INVENTION

1. Field of the Invention

The present invention relates to methods and to analytical systems for performing fibrinogen assays.

2. Discussion of The Background

Blood clotting reactions, in general, employed as clinical assays, measure the time required for the formation of a fibrin clot. Blood clotting assays are principally used for screening, diagnosis, and for monitoring patients receiving anticoagulant therapy.

There are many types of coagulation assays. These include: prothrombin time (PT); partial thromboplastin time (PTT); activated partial thromboplastin time (APTT); fibrinogen assay (i.e., the measurement of the concentration of clottable fibrinogen in a sample); thrombin time, also known as thrombin clotting time (TCT); activated clotting time (ACT); etc. The most frequently performed of these assays is prothrombin time.

The determination of the concentration of clottable fibrinogen in plasma is important for the investigation of coagulation disturbances in patients. Both immunological methods and coagulation tests have been used for the determination of fibrinogen. The immunological methods display severe diagnostic disadvantages and have consequently not achieved practical importance.

In coagulation tests, the fibrinogen content is determined by the time required for coagulum formation. The most important of these methods is the method of Clauss (see *Acta Haemat.* (1957) 17: 237-246).

In the Clauss method, a diluted plasma, i.e., a weak fibrinogen solution, is mixed with a concentrated thrombin solution, the amount of thrombin being about 550 U ml$^{-1}$ of plasma. With the help of a calibration curve, the fibrinogen content of the sample is correlated to the time taken for the visible appearance of a coagulum. Coagulation tests in which one records photometrically the formation of turbidity during the course of coagulation are also known. See, e.g., Ratge et al, *Clin. Chem.* (1987) 33 (3): 420.

Finally, quantitative methods are also known in which the coagulum formed is isolated and its protein content determined. In this approach, the sample is reacted with thrombin and the coagulum formed isolated, washed and then dried. The protein content of the coagulum or its weight is then determined.

Becker et al (U.S. Pat. No. 4,692,406) disclose a method for the simultaneous determination of fibrinogen and of fibrinogen fission products in plasma. This method uses a snake venom enzyme with thrombin-like activity. In this method, the period of time between the addition of the enzyme and commencement of turbidity formation, which is a measure of the amount of fibrinogen fission products, is measured. The speed of turbidity formation is subsequently measured to determine the amount of fibrinogen present in the sample.

The prothrombin time test and the activated partial thromboplastin time test are each commonly used clinical tests to determine a patient's ability to form clots. These tests, and the other tests noted above are extensively used by hospitals, clinics, and laboratories for preoperative evaluations and for anticoagulant therapy administered to cardiac patients, among other patients. These tests are each based upon time measurements, and for the most part measure what is called an end point or clotting time, which occurs when fibrinogen is being polymerized to fibrin.

Many of these types of assays monitor change in sample optical density to measure the reaction. See, for example, Natelson et al (*Am. J. Clin. Path.* (1974) 61(6): 828-833), Lipscomb (U.S. Pat. No. 4,720,787), Saito et al (U.S. Pat. No. 4,217,107), Baughman et al (U.S. Pat. No. 4,289,498), Gross et al (U.S. Pat. No. 3,458,287), Eichelberger et al (U.S. Pat. No. 4,047,890), Becker et al (U.S. Pat. No. 4,692,406), Callahan et al, "Semiquantitative Fibrinogen Determination From the PT Clotting Reaction", Tech. Bulletin Tech. THR8804, copyright 1988 by Organon Teknika, Durham, N.C., USA, and Carroll et al "The Clot Signature and New Aspects in Coagulation Testing" July 1989, Ortho Diagnostic Systems Inc, Raritan, N.J., USA.

In addition to being assayed by the coagulation rate method as in the Clauss method noted above, fibrinogen can be assayed by the coagulation rate as in the Clauss method modified by Vermylen et al (*Clin. Chem. Acta* (1963) 8:418-424), or by sulfite precipitation, Rampling et al. (*Clin. Chem. Acta* (1976) 67:43), or by the total coagulable fibrinogen method of Ratnoff et al (*J. Lab. Clin. Med.* (1951) 37:316-320), or by an assay system based on the turbidity rate measurement of the conversion of fibrinogen to fibrin polymer sold by Du Pont (Du Pont Aca TM, Du Pont Clinical Systems, Wilmington, Del. USA). The Vermylen et al method uses a glass hook or platinum loop which is continuously moved in and out of the clotting mixture until the appearance of a fibrin web as the end-point.

Today, there are 750,000 cases of acute myocardial infarction in the U.S. annually and more than one million combined cases of other arterial embolic events, pulmonary embolism (PE) and deep vein thrombosis (DVT). Approximately 25% to 35% of these cases are potential candidates for thrombolytic therapy. This therapy consisting of intravenous administration of a fibrinolytic drug to promote the dissolving of the occluding blood clot will be applied in many small community hospitals.

There currently exists a 0.5% rate of intracranial bleeding and from 1% to 20% rate of significant extracranial bleeding. At present, no convenient, reliable and rapid diagnostic instrument is available to follow the patient.

A challenge which is now emerging is how to better control thrombolytic therapy to maximize effectiveness and minimize risk of bleeding problems. Although no single diagnostic assay thus far appears to be the answer to this challenge, integration of a combination of diagnostic assays and other indicators could improve therapy.

Fibrinogen measurement, while difficult to achieve at the bedside accurately and conveniently, is an important parameter in thrombolytic therapy, particularly with regard to assessment of bleeding risk and therapeutic management of bleeding once it occurs. The measurement of initial fibrinogen drop, even that associated with fibrin selective agents, such as recombinant tissue plasminogen activator (rt-PA), would also be useful confirmation that the lytic process has begun. This is equally important for other fibrin selective agents such as streptokinase, urokinase, and anistreplase, since these drugs work by means of a systemic lytic effect.

With existing prior art methods for fibrinogen determination, centrifugation of the blood is necessary before performing the assay, because the blood cells interfere with the measurement. Separation of the blood cells takes time and increases the overall time required for the assay. If a fibrinogen assay can be performed as soon as the blood is collected, in vitro artifacts which arise from plasmin activation (due to the action of thrombolytic drugs) should minimally, if at all, affect test results.

These artifacts arise from the action of plasmin on a variety of proteins associated with blood coagulation including fibrinogen itself. This occurs in vitro after the blood sample has been collected. A delay of even several minutes (currently at least fifteen minutes with existing methods) produces inaccurate results. One solution to this problem has been to use inhibitors of plasmin or plasminogen activator as an additive to the blood collection tube to preserve the sample prior to testing. The use of inhibitors, however, adds additional expense and also restricts the field of functional assays which may be performed subsequently on the sample.

As noted supra in the past, with streptokinase, thrombin time testing had been employed to establish the presence of a lytic effect in DVT and PE where antibodies to streptokinase could neutralize a portion of the effect. A convenient, rapid, and accurate fibrinogen assay capable of being performed by the addition of one drop of whole blood to a dry chemistry test card would be a significant improvement in current diagnostic potential and could go a long way toward optimizing thrombolytic therapy for a particular patient. In addition, the diagnostic capacity of such a system could aid in clinical trials of the many newly emerging thrombolytic drugs currently in development. There is thus a clear need for such an assay.

SUMMARY OF THE INVENTION

Accordingly, it is an object of this invention to provide a simple and accurate method, and an analytical system, for performing a fibrinogen assay, including a fibrinogen screening test, which does not suffer from the disadvantages noted above.

It is another object of this invention to provide a method, and an analytical system, for performing a fibrinogen assay, including a fibrinogen screening test, requiring no preparation of a reagent-containing solution.

It is another object of this invention to provide a method, and an analytical system, for performing a fibrinogen assay, including a fibrinogen screening test, which minimizes problems associated with reagent instability.

It is another object of this invention to provide a method, and an analytical system, for performing a fibrinogen assay, including a fibrinogen screening test, requiring only a very small amount of sample.

It is another object of this invention to provide a method, and an analytical system, for performing a fibrinogen assay, including a fibrinogen screening test, which does not require prior separation of a plasma sample and may be performed on whole blood.

Surprisingly, all of these objects, and other objects which will become apparent from the description of the invention provided hereinbelow, have all been discovered to be satisfied with the present method and by the present analytical system for performing fibrinogen assays.

In a first illustrative embodiment, a kinetic method for determining the clottable fibrinogen level in a blood or blood-derived sample (a fibrinogen assay) is used. This method comprises, in its basic elements, the following steps:

(i) subjecting to an oscillating magnetic field a dry reagent matrix in which is embedded a plurality of magnetic particles distributed homogeneously throughout the reagent matrix, wherein the reagent is one member selected from the group consisting of fibrinogen assay reagents;

(ii) adding a volume of a whole blood or blood-derived sample to the reagent, causing it to become solubilized and freeing the particles to move in an oscillating pattern induced by the oscillating magnetic field;

(iii) optically monitoring said reaction chamber to measure the maximum amplitude of said particle oscillation, A, and the subsequent residual, post peak minimum amplitude, B, of said particle oscillation; and (iv) using at least B to measure fibrinogen concentration in said sample.

In a second illustrative embodiment, an end-point method of performing a fibrinogen assay is used. This method comprises, in its basic elements, the following steps:

(i') subjecting to an oscillating magnetic field a dry reagent matrix in which is embedded a plurality of magnetic particles distributed homogeneously throughout the matrix, wherein the reagent is one member selected from the group consisting of fibrinogen assay reagents;

(ii') adding a volume of a whole blood or blood-derived sample to the reagent, causing it to become solubilized and freeing the particles to move in an oscillating pattern induced by the oscillating magnetic field;

(iii') optically monitoring the oscillation of the particles to measure a start time and a stop time for the fibrinogen assay corresponding to a change in the degree of particle movement relative to the magnetic field; and (iv') using the start time and the stop time to measure fibrinogen concentration in the sample.

In a variation of the second illustrative embodiment, an end-point method of performing a fibrinogen assay is used. Making reference to FIG. 1, this method comprises, in its basic elements, the following steps:

(i") subjecting to an oscillating magnetic field a dry reagent matrix contained in the reaction chamber (24) of the reaction slide illustrated in the Figure only and not in sample well (22) or conduit (26), in which matrix is embedded a plurality of magnetic particles distributed homogeneously therethrough, wherein the reagent is one member selected from the group consisting of fibrinogen assay reagents;

(ii") adding a volume of a whole blood or blood-derived sample to sample well (22) of the reaction slide, wherein the volume of the sample is chosen such that the sample is delivered to conduit (26) of the reaction slide but does not enter reaction chamber (24) or contact the reagent;

(iii") adding a volume of buffer diluent to sample well (22), the volume of buffer being sufficient to wash the whole blood or blood-derived sample into reaction chamber (24), diluting the sample in the process and transporting it such that the diluted sample is brought into contact with the reagent, causing the reagent to become solubilized and freeing the particles to move in an oscillating pattern induced by the oscillating magnetic field;

(iv″) optically monitoring the oscillation of the particles to measure a start time and a stop time for the fibrinogen assay corresponding to a change in the degree of particle movement relative to the magnetic field; and (v′) using the start time and the stop time to measure fibrinogen concentration in the sample.

The blood-derived samples which may be used in this invention are defined as anticoagulated (i.e., citrated) blood or plasma samples or buffer diluted anticoagulated blood or plasma samples.

In a preferred embodiment, the reaction slide described by Oberhardt in U.S. Pat. No. 4,849,340 and in U.S. Pat. application Ser. No. 07/192,672, filed May 10, 1988, now U.S. Pat. No. 5,110,727 is used. These two documents are hereby incorporated by reference.

BRIEF DESCRIPTION OF THE FIGURES

A more complete appreciation of the invention and many of the attendant advantages thereof will be readily obtained as the same becomes better understood by reference to the following detailed description when considered in connection with the accompanying figures, wherein like reference numerals designate identical or corresponding parts throughout the several views.

DETAILED DESCRIPTION OF THE PREFERRED EMBODIMENTS

Figure 1:
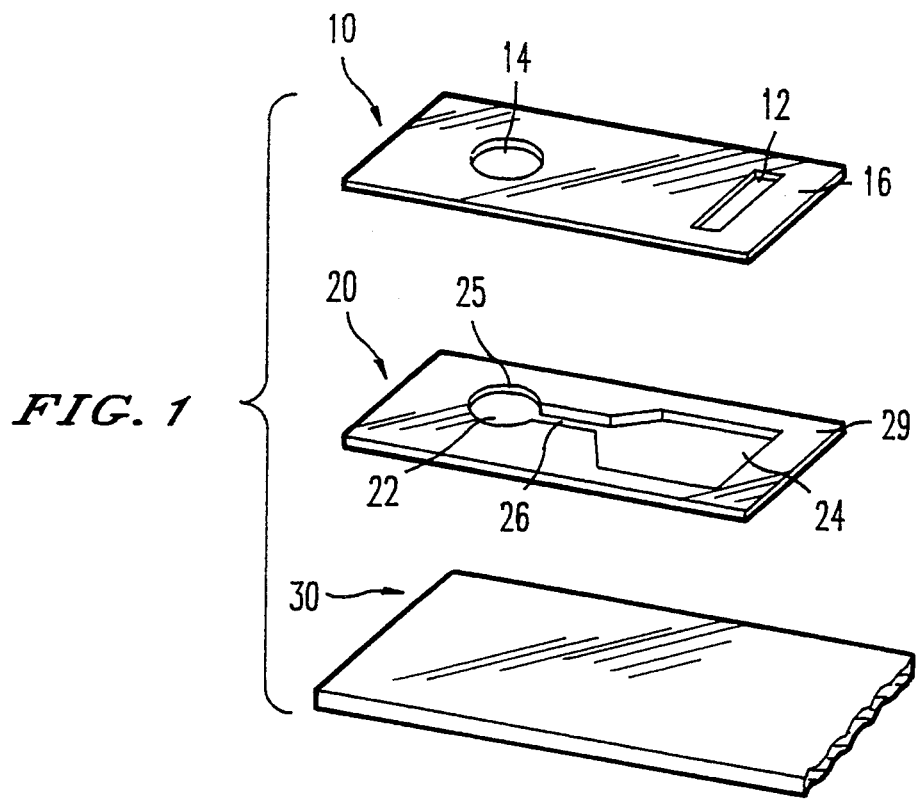
FIG. 1 is an exploded perspective of an assembled reaction slide which can be used in performing the present, end-point or kinetic, methods for measuring the clottable fibrinogen level in a blood or blood-derived sample.

There is a growing need to develop improved diagnostic approaches to aid in administration of thrombolytic therapy. Development of fast-turnaround fibrinogen measurement is one area where definite benefit to the patient could result. In addition, simple, rapid, convenient assay of fibrinogen could have other applications outside of the thrombolytic therapy area such as: in management of post operative bleeding; in preoperative assessment; in patients with liver disease or post liver transplant patients, in disseminated intravascular coagulation (DIC) patients, and as a general tool to assess bleeding at the patient's bedside. The present invention addresses and solves the drawbacks found in such current assay systems.

The present invention provides a novel fibrinogen assay based on monitoring the movement of magnetic particles incorporated in the assay reaction. As noted above, in the present assay, a dry reagent matrix in which is embedded a plurality of magnetic particles, distributed homogeneously therethrough, is subjected to an oscillating magnetic field. This oscillating magnetic field may be obtained by using (1) a stationary oscillating magnet, or (2) a moving permanent magnet, or (3) a combination of an oscillating magnet and a stationary permanent magnet. (See U.S. patent application Ser. No. 07/192,672 for a detailed discussion.)

The whole blood or blood-derived sample is then added to the reagent, causing it to become solubilized simultaneously, thereby freeing the particles to move in an oscillating pattern induced by the oscillating magnetic field. As discussed in detail in U.S. patent application Ser. No. 07/192,672, under the influence of the magnetic field, the freed magnetic particles form columnar structures or stacks, which, under the influence of the oscillating magnetic field, create a flicker phenomena due to a change in the orientation of these columnar structures or stacks.

The oscillation of the particles is optically monitored by subjecting the particles to incident light and detecting reflected (scattered) light rays. Before the sample is added to the dry reagent matrix, the magnetic particles which are entrapped in the dry reagent matrix are incapable of oscillation. After the magnetic particles are freed by addition of the sample to the dry reagent matrix, a maximum number of particle-based columnar structures or stacks can quickly be observed to oscillate to the greatest degree, providing a maximum oscillation amplitude, shown as A in FIG. 3. As the reaction progresses, a coagulum forms restricting the degree of oscillation of an increasing number of particle-based columnar structures or stacks. This gradual decrease in the flicker pattern produces a residual post-peak minimum amplitude, shown as B in FIG. 3.

In the present assay, either the degree of particle movement relative to said oscillating magnetic field is monitored to measure the start time and stop time of the assay, or one or more features of the kinetic curve, other than clotting time, is/are used to measure fibrinogen concentration in the sample.

In the blood coagulation monitoring system described, it is thought that higher fibrinogen levels produce denser fibrin clots which would restrict particle oscillation to a greater degree thereby resulting in a lower minimum oscillation signal after the peak signal. As may be seen in FIG. 4, the clotting curve is complex. Starting at 1, the first indication of particle oscillation is apparent. The magnitude of magnetic particle oscillation is apparent. The magnitude of magnetic particle oscillation as monitored optically increases from the start of the assay at 1 and peaks at 2 and 2′ on the upper and lower portions of the wave envelope, respectively.

Figure 4:
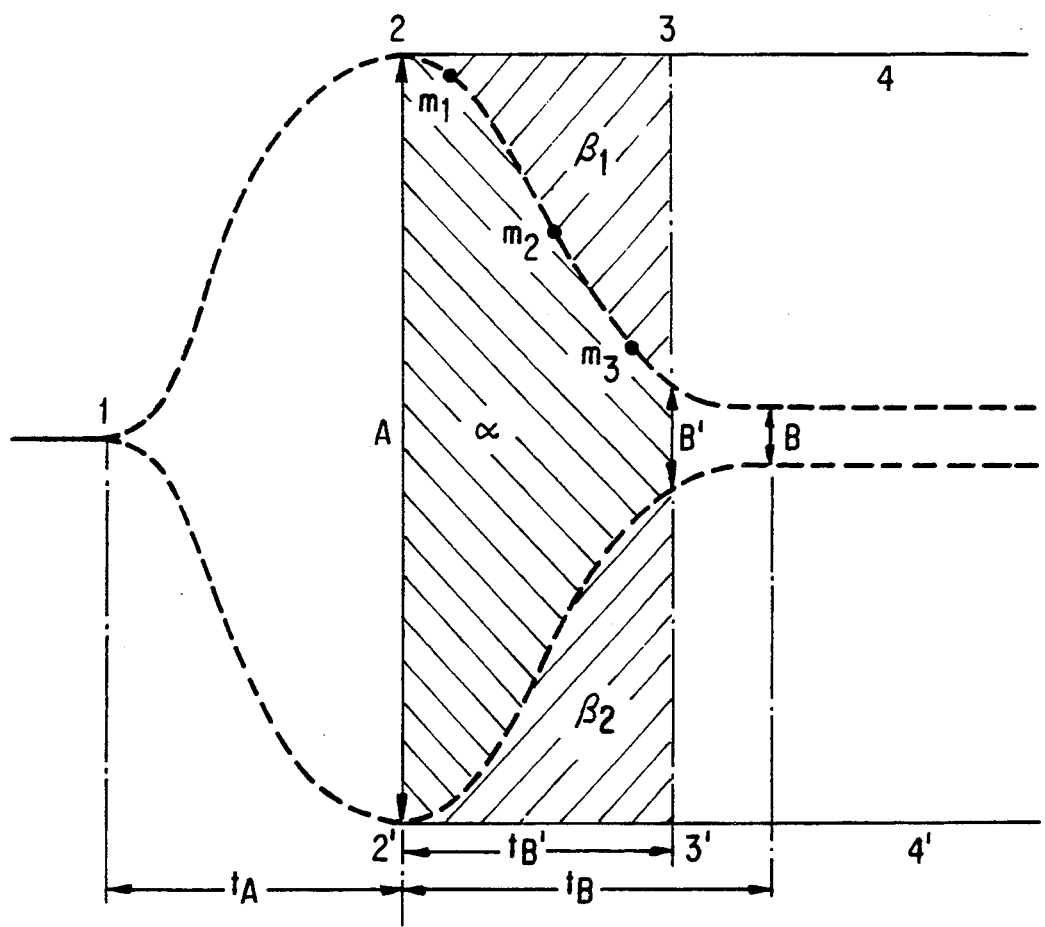
FIG. 4 shows additional features of the kinetic clotting waveform which may be utilized as parameters to construct specific algorithms to measure fibrinogen.

The oscillation signal amplitude at the peak is designated as A and shown in FIG. 4 as a signal difference between 2 and 2′. The time at which A occurs, $t_A$, is the clotting time. Tracing along the waveform envelope at the top, the amplitude decreases after $t_A$.

Three points $m_1$, $m_2$, and $m_3$ are shown. Points $m_1$ and $m_3$ are chosen at arbitrary but fixed times. Point $m_2$ is chosen as an inflection point. The slope of the curve taken at $m_1$, $m_2$ or $m_3$ can be utilized as a measure of fibrinogen, since these slopes are steepest (most negative) at the highest fibrinogen levels and become less steep with decreasing fibrinogen.

After $m_3$, the oscillation signal amplitude continues to decrease with increasing time, eventually approaching an asymptotic value B. Fibrinogen concentration is proportional to A/B and to (A−B)/A. Fibrinogen concentration is also inversely proportional to B and directly proportional to A−B, but these parameters alone are generally less precise than A/B or (A−B)/A.

Other, more precise, measures of fibrinogen concentration are areas obtained by integrating portions of the kinetic curve. For example, the area bounded by: a straight line extending between 2 and 2' of length or amplitude A at the left; amplitude B' at the right (where: B' is the amplitude of the curve at the time $t_{B'}$; and $t_{B'}$ is taken typically at a time between 10 seconds after $t_A$ and up to 90% of $t_B$ but more typically at 60% of $t_B$) and the area defined by the waveform envelope at the top and bottom is designated as $\alpha$ and is inversely proportional to fibrinogen concentration in the sample.

Another area, designated as $\beta$ may be utilized. $\beta$ is equal to the area of the rectangle with sides of magnitude A and opposite sides of magnitude $t_B$, minus the area designated as $\alpha$. $\beta$ is shown in FIG. 4 as consisting of two portions: an upper portion, $\beta_1$ and a lower portion, $\beta_2$. The line extending through amplitude B' and intersecting parallel lines 4 and 4' constructed as perpendiculars to the line of magnitude A at points 2 and 2° helps to define the right boundary of $\beta$. $\beta$ is directly proportional to fibrinogen concentration and is very precise.

$\beta$ and $\alpha$ may also be used in combination, i.e., taken as a ratio or difference to indicate fibrinogen level. In addition $\alpha$ and/or $\beta$ could be calculated independently of time, for example by always using $t_B$ as the horizontal measure for area calculation (see FIG. 4).

Figure 5:
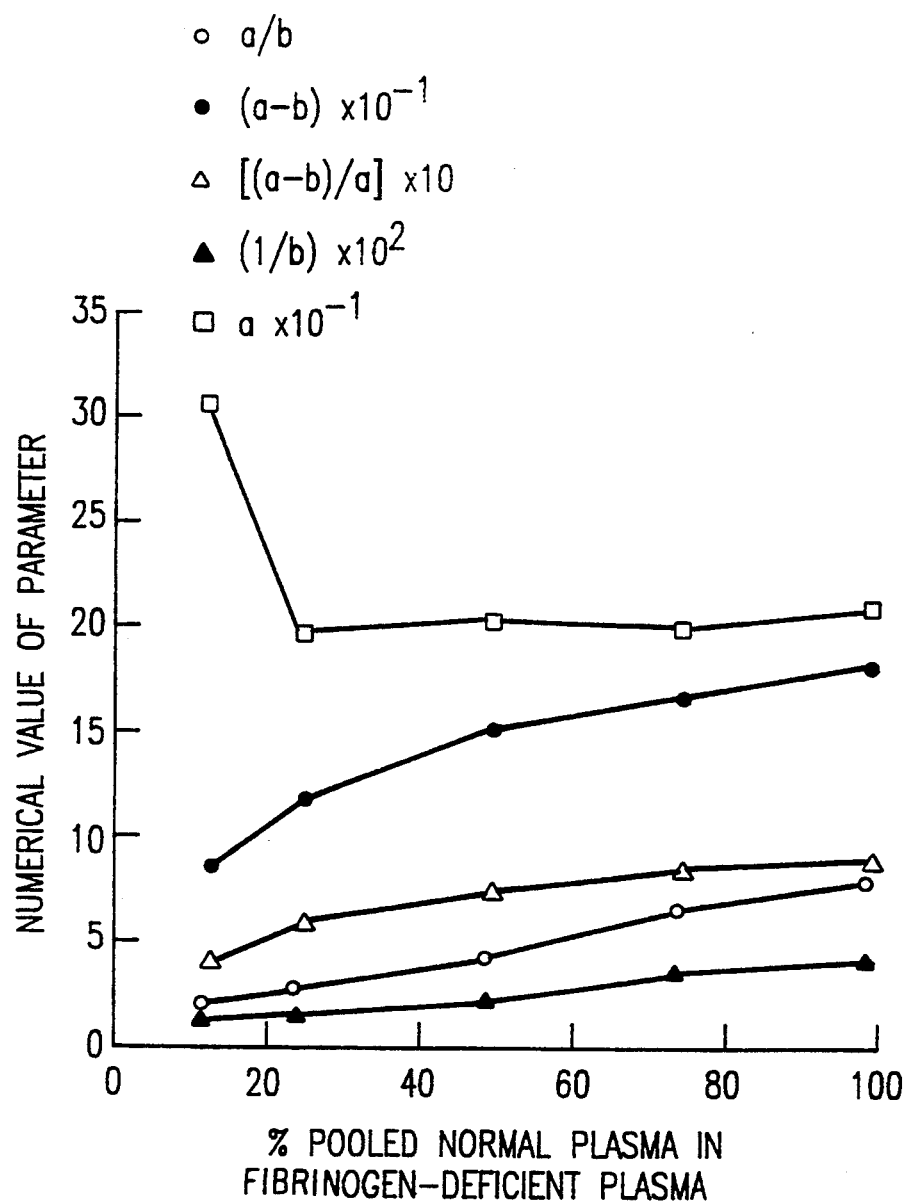
FIGS. 5, 6 and 7 are comparisons of the feature-based algorithms for the fibrinogen assay.

FIG. 5 shows how some of the kinetic parameters of the clotting curve vary with concentration of fibrinogen for a dry reagent slide incorporating reptilase and a citrated plasma sample consisting of pooled normal plasma diluted in varying amounts in fibrinogen deficient plasma.

The present invention thus provides fibrinogen measurement using magnetic particle dry chemistry technology. Using this approach fibrinogen can be measured with each of the approaches listed below.

Although a capillary slide geometry, such as that of the reaction slide described in either U.S. Pat. No. 4,849,340 or U.S. patent application Ser. No. 07/192,672, now U.S. Pat. No. 5,110,727, is ideally suited for creating a properly patterned format, housing the reagent, and monitoring the sample, the assay of the present invention will work perfectly well by simply adding a premeasured amount of dry reagent containing magnetic particles to any solid surface (e.g., a microtiter plate well or substantially flat surface).

It is important that the dry reagent be prepared such that it is rapidly dissolved upon the addition of the blood or blood-derived sample. Freeze-drying on a surface, or even better, between two surfaces closely apposed at a capillary or near capillary distance works best. This produces a mass of low matter content which enables rapid sample penetration and dissolution.

Although freeze drying provides excellent results for preparation of the dry magnetic particle-containing reagent, room temperature, vacuum, desiccant, convective, or other types of drying can also be used to achieve good results. For example, room temperature drying of reagent on the base of a reaction slide (with spacer in place) followed by attachment of the cover can be used to obtain a self-metering dry reagent containing element.

Figure 2:
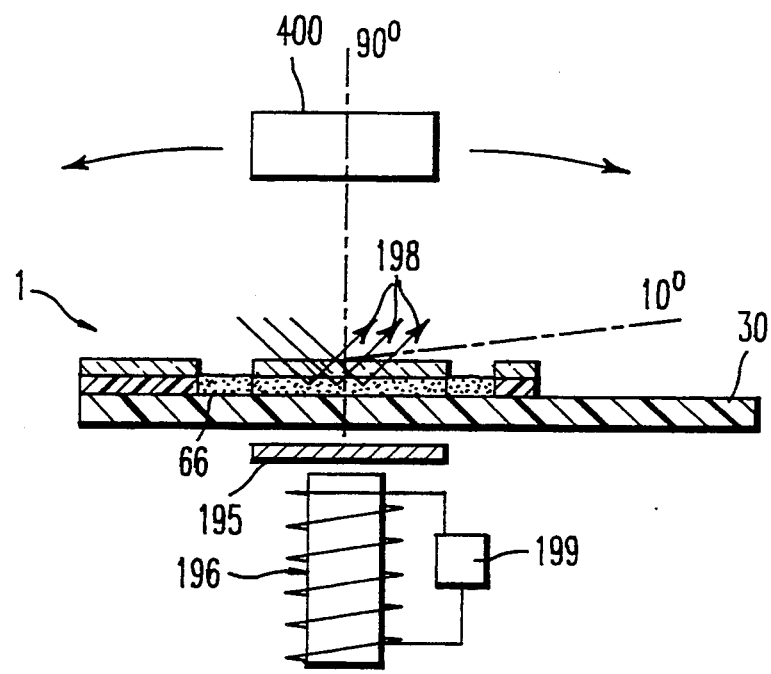
FIG. 2 is a longitudinal vertical cross-section of a reaction slide together with apparatus for using magnetic particles to measure the reaction.

In a preferred embodiment the reaction slide illustrated in FIGS. 1 and 2 is used. FIG. 1 is an exploded view showing the relative position of the cover (10), overlay (20) and base (30) components of the slide. Cover (10) comprises a thin glass or polymer sheet transparent to light, having formed therein a sample receiving opening (14) and an elongate opening (12) proximate to distal end (16) of the cover.

Overlay (20) comprises a thin glass or polymer sheet, typically transparent, having formed therein a cut-out, the cut-out having a geometry essentially as shown to form a sample well (22), a reaction chamber (24) and an optional conduit (26) communicating the reaction space and the sample receiving opening.

Thus the cut-out of overlay (20) can either have a geometry forming sample well (22) and reaction chamber (24) in communication with each other, or a geometry comprising sample well (22), reaction chamber (24), and conduit (26) essentially as shown.

Reaction chamber (24) becomes a reaction volume upon assembly of the cover, overlay and base. Advantageously, tapering walls (25) form a transition between conduit (26) and sample well (22) or if conduit (26) is not used, and reaction chamber (24). The distal end of the overlay is closed as shown at (29).

The base (30) comprises a sheet of glass or polymer material, which is typically somewhat thicker than either the cover (10) or overlay (20).

As shown in the figure, the length (left to right in the drawing) of cover (10) is approximately the same as that of overlay (20), and the width (top to bottom in the drawing) of cover (10) and overlay (20) are about the same and typically less than that of base (30). When the cover, overlay and base are assembled, the bottom surface of cover (10), facing base (30), is spaced from the top surface of base (30) by a distance that is sufficiently small to cause a volume of sample corresponding to the volume of the reaction chamber to be drawn simultaneously into the reaction volume by capillary action. This action is made possible by the presence of vent (12). In use reaction chamber (24) is charged with the dry reagent containing the magnetic particles homogeneously dispersed therethrough.

FIG. 2 provides a longitudinal vertical crosssection of the reaction slide together with an apparatus for using the magnetic particles to measure the assay. In this figure, reaction slide 1 is disposed and in close proximity to a permanent magnet (195). Beneath the permanent magnet (195) is an electromagnet (196) which is driven by power supply (199) for cycling voltage on and off at a desired frequency. In the practice of the present invention it is possible to use the permanent magnet above (without the electromagnet), creating an oscillating magnetic field with the permanent magnet by moving the permanent magnet back and forth along a plane essentially parallel to the plane of the reaction slide. In another embodiment the electromagnet above is used to generate an oscillating magnetic field. In still another embodiment, both of these magnets are used essentially as shown in the figure.

A light source such as an infrared light emitting diode is appropriately situated for providing incident light on the reaction chamber and a detector positioned for detecting light rays reflected from the sample within the reaction volume 66. The reflected rays, illustrated as rays (198), are detected by detector (400). Detector (400) can be positioned at any position which will permit it to detect the reflected (scattered) rays, but a position between the 90° and the 10° position, inclusively, is preferable, with a position between the 90° and 45° position being preferred, and between 90° and 75° being most preferred.

Clot formation kinetic approaches

Along with buffers sufficient to control pH in the ranges known in the art (typically 7.0 to 7.4), the reagent used in this embodiment contains (a) thromboplastin present in an amount sufficient to cause coagulation of normal plasma with near minimal B values (PT test) plus magnetic particles, typically 8.3 mg ml$^{-1}$ but variable over a wide range (see U.S. Ser. No. 07/192,672); (b) thrombin plus magnetic particles in amounts similar to that used in (a) above defined functionally; or (c) a snake venom, e.g., reptilase, copperhead venom enzyme, or Malayan pit viper venom enzyme in amounts similar to (a) above, as defined functionally for the venom plus magnetic particles in amounts described in (a) above. The blood sample does not normally require dilution and may be added directly to the dry chemistry assay mixture. Some dilution, to within 1:2 (by volume) and most preferably not more than 1:4 (by volume) is, however, possible with this embodiment, and may be used if desired. In some cases, dilutions as great as 1:10 (by volume) or even 1:20 (by volume) could be employed advantageously, for example at very high fibrinogen levels.

It should be recognized that a variety of thrombin preparations exist. Actual purity and activity may vary depending upon the source. In addition to human thrombin, bovine thrombin is often used. In addition to source and activity variations, lot-to-lot variability also occurs. The same is true for the snake venoms. Here, lot-to-lot activity can vary considerably. Thromboplastins are also quite different, depending upon the source: rabbit brain, ox brain, human brain, etc. In addition, lot-to-lot variability of thromboplastin from the same source is well known in the blood coagulation diagnostics field.

For this reason the exact amounts of the various clotting reagents employed in formulating suitable dry reagents for use in combination with magnetic particles cannot be specified, but rather the quantities of these clotting reagents are determined functionally as described for each embodiment. The buffer type and concentration may be less important than the pH. Buffers which are commonly employed in blood coagulation reactions may generally be used. Owrens, HEPES, and Tris are among these.

For a reptilase based reagent at pH 7.3, for example, 25 mM HEPES performs better (gives a steeper response curve) than 25 mM Tris. However, other factors can affect performance, for example additives which will now be discussed. Furthermore, optimum pH and buffer selection may depend somewhat upon the type of clotting reagent (fibrinogen assay reagent) and possibly upon the particular lot of reagent chosen. It is generally useful to employ a pH in the range of 7.0 to 7.4 and optimize from there. It is also expedient to use certain additives to improve dissolution characteristics of the dry reagent and to better disperse the magnetic particles upon solubilization. Bovine serum albumin and/or polyethylene glycol in amounts less than 1 wt. % in the reagent formulation work well. The exact amounts may depend upon the properties of the clotting reagent and may differ with each lot number.

Figure 3:
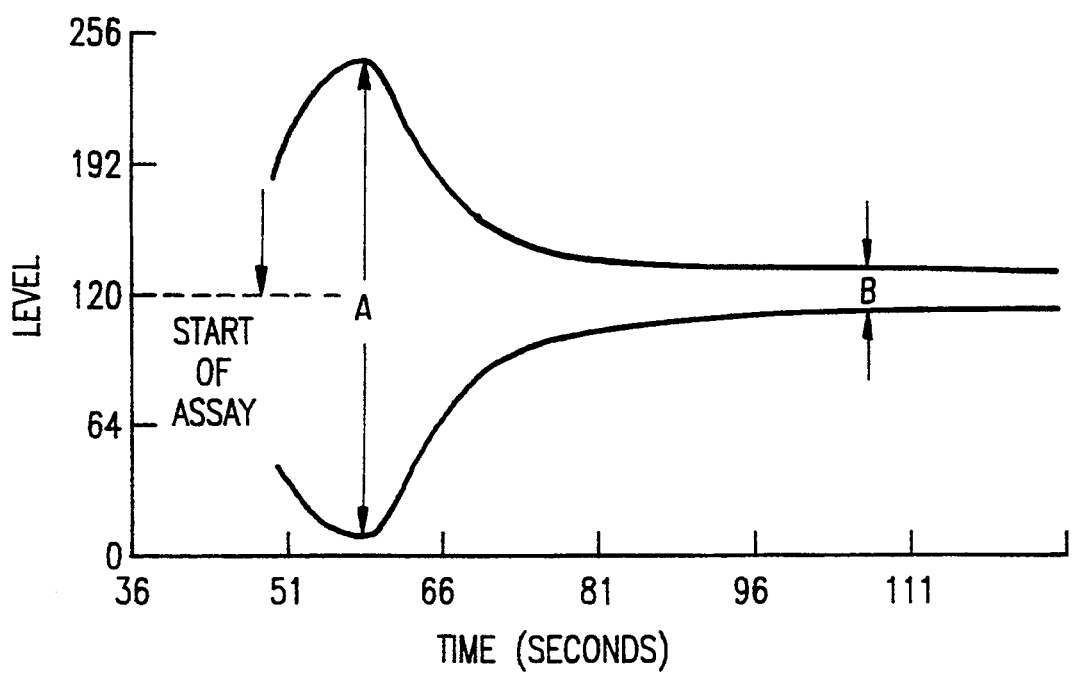
FIG. 3 illustrates the clotting curve for the fibrinogen assay, with A designating the maximum amplitude of particle oscillation and B designating the subsequent residual post peak minimum amplitude of particle oscillation.

To measure fibrinogen using the clot formation kinetics, clotting time is preferably not used. Instead, kinetic parameters reflecting features in the clotting curve (shown FIGS. 3 and 4) are utilized. It should also be noted that whereas thromboplastin based reagent may be utilized to measure fibrinogen in a blood sample using kinetic parameters, this type of reagent is generally not suitable for use with clotting time (e.g., Clauss type) methods. In FIG. 3, A is the peak height maximum (maximum oscillation amplitude), B is the minimum (residual post peak minimum) which is observed after A is reached.

Either A and B, or B only, are used to determine a factor proportional to fibrinogen concentration in the sample. The following measures may be employed: (i) B alone; (ii) A/B (or B/A ); (iii) A−B; or (iv) (A−B)÷A or A÷(A−B). Alternatively, (v), as may be seen in FIG. 4, the negative slope (e.g., at or near the inflection point) between A and B can be utilized. Yet another alternative, (vi), as may be seen in FIG. 4 is the area enclosed by the clotting curve. This area may be bounded by vertical axes at the peak (A) and at a set time after A, e.g., 45 seconds, where: A is normalized and thus made equivalent for each separate assay curve.

Clotting time approaches (Clauss type)

Along with buffers in amounts sufficient to control pH the reagent used contains (a) thrombin plus magnetic particles, where the thrombin concentration is sufficient to cause coagulation of normal plasma with B values somewhat above the absolute minimum obtained at ever increasing thrombin concentration and the magnetic particle concentration is typically 8.3 mg ml$^{-1}$, but can be varied over a wide range (see U.S. patent application Ser. No. 07/192,672) or (b) a snake venom enzyme in place of thrombin under essentially the same conditions and in amounts sufficient to produce the same functional effects (e.g., reptilase, (a thrombin-like enzyme isolated from the venom of *Bothrops atrox*), copperhead venom enzyme, (*Agkistrodon contortrix*) or Malayan Pit Viper venom enzyme (*Agkistrodon rhodostoma*) (see Becker et al, *Thromb. Res.* (1984) 35:475–484 and U.S. Pat. No. 4,692,406) plus magnetic particles in amounts described in (a) above. In this embodiment the blood sample to be analyzed is first diluted with a buffer (typically Owens buffer) and then added to the dry chemistry assay mixture in an appropriate analyzer. Clotting time is then measured.

For the Clauss type methods (clotting time based) dilution of the sample is necessary to achieve sufficient dynamic range, as discussed by Vermylen et al. *Clin. Chim. Acta*, (1963) 8: 418–424. In the present system, this is achieved by sample predilution or may be conveniently achieved by placing a fixed small volume of sample in conduit (26) in FIG. 1 of the reaction slide.

For example, 1 to 3 microliters of sample is carefully pipetted into sample well (22) near the opening of conduit (26) to deliver the entire sample into conduit (26). Actually, once delivered into the appropriate region of sample well (22) by the pipette, the sample will automatically be taken up into conduit (26) via capillary action. In this type of reaction slide, there must not be any clotting reagent (thrombin, etc.) in conduit (26). The dry reagent must be confined to reaction volume (24). This is easily achieved in manufacture of the dry chemistry reaction slide in a number of ways, such as by filling from the vent area forward. It is preferred not to use more than 3 microliters of sample in a reaction slide as shown in FIG. 1 with a total volume (excluding sample well and vent area) of 25 microliters, because any more than this cannot become effectively diluted in the next step. It is not recommended to use less than 1 microliter of sample, since the sample must be accurately pipetted in this embodiment (but not in the previously described kinetic method). It is difficult to achieve accurate and convenient transfer of less than 1 microliter of sample with current pipetting technology.

After the sample is in place, a fixed volume of buffer diluent is added to the sample well in a volume equal to or preferably in excess of the volume required to fill conduit (26) plus reaction chamber (24). For a 25 microliter capacity reaction slide, a volume of 25 to 50 microliters of buffer diluent is effective, with a volume of 30 to 40 microliters preferred. Less than 25 microliters could give rise to inadequate flow, particularly if the reaction volume does not completely fill. More than 50 microliters of diluent may overflow the sample well in a reaction slide of this size.

As soon as the sample is washed into the reaction volume, and diluted in the process, the dry chemistry starts to become solubilized, and the clotting reaction begins. The range of dilutions achieved would be from approximately 1 in 25 (by volume) for 1 microliter of sample to 3 in 25 (by volume) for a 3 microliter sample. Over this range, it is possible to select a concentration of clotting reagent and appropriate dilution factor to provide a good standard curve which is essentially linear on log-log paper for a plot of clotting time ($t_A$) versus the concentration of fibrinogen.

This curve may then be utilized as a reference, as in the conventional Clauss assays to quantify unknown samples on the basis of clotting time. It is also possible to select clotting endpoints other than $t_A$. For example, if an adjusted endpoint amplitude of, for example, 0.9 A is selected (after the peak amplitude A is reached) good results may be obtained by using the time at which 0.9 A occurs as clotting time. The same is true for 0.85 A, however, this cannot be pushed too far, otherwise sensitivity at low fibrinogen levels will be lost, especially if the lowest level of fibrinogen which is desired to be detected produces a B value equivalent or nearly equivalent to the adjusted endpoint amplitude. One advantage of utilizing adjusted endpoint amplitudes is that the slope of the straight line logarithmic fibrinogen standard curve may be made steeper.

It is also possible to prepare a reaction slide containing dried reagent consisting of magnetic particles and buffer and a binding agent such as less than 1 wt. % bovine serum albumin or polyethylene glycol (molecular weights ($\overline{Mw}$) of polyethylene glycol ranging from approximately 3,400 to 10,000 daltons have been successfully employed) or a combination of both. To this reaction slide, a 1 to 3 microliter sample is added to conduit (26) of the reaction slide via sample well (22). In this case, a diluted thrombin or snake venom is employed to wash the sample as before, into reaction volume (24) diluting it on the way. The dry chemistry, in this case the magnetic particles plus other reagents, becomes solubilized and provides an adequate clotting endpoint. This variation of the methodology is, however less convenient because it requires reagent preparation by the user and may not provide as precise a starting point.

A logarithmic relationship exists between clotting time measured this way and fibrinogen concentration in the sample. This relationship is used, with comparison to appropriate fibrinogen standard solutions, for analysis of unknown concentrations of fibrinogen in blood samples (either citrated whole blood or citrated plasma).

Yet another possible configuration is to prepare a reaction slide containing clotting reagent (thrombin, snake venom, or thromboplastin) mixed with magnetic particles, buffer, and a binding agent, such as less than 1 wt. % bovine serum albumin or polyethylene glycol, wherein the mixture is in dry form and at greater concentration (4 to 8-fold) than typically used but contained in a proportionally smaller volume such that this volume is situated in conduit (26) of the reaction slide and the remaining portions of the reaction slide are empty. Very good results may be obtained with this type of reaction slide configuration as follows. First, a defined quantity (2 or 3 microliters) of distilled water is added to sample well (22) near conduit (26). This water is rapidly taken up by conduit (26) via capillary action. After a brief incubation period (typically 5 to 30 seconds, depending upon the concentration and types of reagents employed) a volume of previously diluted sample which is sufficient to fill the remainder of the reaction volume (24) is applied to sample well (22). This sample (either plasma or whole blood typically diluted 1:10 (by volume) in buffer) mixes with the reagent solution and magnetic particles in conduit (26), and the resultant mixture rapidly enters reaction volume (24) whereupon a signal is detected initiating the reaction monitoring sequence. Then, B alone, A/B or its reciprocal, $(A-B) \div A$ or its inverse, $A-B$, negative slope, normalized area, and in the case of thrombin or snake venoms, also clotting time, may be measured to provide a fibrinogen assay.

Fibrinogen screening tests (clotting time based)

Along with buffers, the reagents used in this embodiment contain (a) thrombin plus magnetic particles or (b) a snake venom (e.g., reptilase copperhead venom enzyme, or Malayan pit viper venom enzyme) plus magnetic particles. The blood sample should not be diluted and is added directly to the dry chemistry mixture. Clotting time is then measured. When thrombin is used, the result is reported as a thrombin time (TT) or thrombin clotting time (TCT). When reptilase is used, the result is reported as reptilase time. These screening tests are generally useful to determine that fibrinogen is abnormal.

In a first (kinetic) preferred embodiment, the present method for measuring the clottable fibrinogen level in a blood or blood-derived sample (performing a fibrinogen assay) comprises the following steps (i) to (iv).

(i) Subjecting to an oscillating magnetic field a reaction slide bearing (1) a sample well for receiving a liquid sample and (2) a reaction chamber containing a dry reagent matrix in which is embedded a plurality of magnetic particles distributed homogeneously throughout the reagent matrix, there the reagent is one member selected from the group consisting of fibrinogen assay reagents.

(ii) Adding a whole blood or blood-derived sample to the sample well whereby the sample is introduced simultaneously to the reaction chamber, the reagent is solubilized and the particles are freed to move in an oscillating pattern induced by the oscillating magnetic field.

(iii) Optically monitoring the reaction chamber to measure the maximum amplitude of particle oscillation, A, and the subsequent residual post peak minimum amplitude, B, of the particle oscillation.

(iv) Using at least B or an area defined by the kinetic clotting curve between A and B to measure fibrinogen concentration in the sample.

In the first preferred embodiment the dry reagent matrix comprises thromboplastin, thrombin or reptilase.

In another preferred embodiment, the fibrinogen assay may be based on clotting time using a thrombin or reptilase based reagent and start and stop time for the assay.

In this second (end-point) preferred embodiment the method of performing a fibrinogen assay comprises the following steps (i') to (iv').

(i') Subjecting to an oscillating magnetic field a reaction slide bearing (1) a sample well for receiving a liquid sample and (2) a reaction chamber containing a dry reagent matrix in which is embedded a plurality of magnetic particles distributed homogeneously throughout the reagent matrix, where the reagent is one member selected from the group consisting of fibrinogen assay reagents.

The sample well and reaction chamber are in fluid connection through a transport zone of geometry such that a volume of liquid analyte sample placed in the sample well and corresponding to the volume of said reaction chamber is transported from said sample well to said reaction chamber simultaneously.

(ii') Adding a whole blood or blood-derived sample (e.g., 2 to 20 fold diluted (by volume) in Owrens' buffer) to the sample well whereby the sample is introduced simultaneously to the reaction chamber, the reagent is solubilized and the particles are freed to move in an oscillating pattern induced by the oscillating magnetic field.

(iii') Optically monitoring the reaction chamber to measure a start time and a stop time for the fibrinogen assay, corresponding to a change in the degree of particle movement relative to said magnetic field.

(iv') Using the start time and the stop time to measure fibrinogen concentration in the sample.

FIG. 5 provides five curves, each curve representing a different kinetic parameter obtained from the clotting curve produced by a reptilase based dry reagent. The legend indicates which curve corresponds to each parameter. FIG. 4 can be used to help in understanding the relationship of the parameters to clotting kinetics. On the graph, the numerical value of the parameter is the ordinate. The percent of pooled normal plasma (PNP) diluted in fibrinogen deficient plasma used to obtain the clotting kinetics from which the parameters were determined is the abscissa.

From the data shown in FIG. 5, it is observed that a variety of parameters show proportionality to the fibrinogen level.

From a comparison of these parameters, A alone is relatively poor as a determinant of fibrinogen level, because it does not show significant differences from 100% through 25% PNP. Of the remaining four, (A−B)/A and A/B have generally been the most precise parameters, with A/B showing better precision at the lowest fibrinogen concentrations measurable with this system. (A−B)/A is generally the more precise parameter of higher fibrinogen levels. It should be recognized that (A−B)/A is equal to 1−(B/A).

Figure 6:
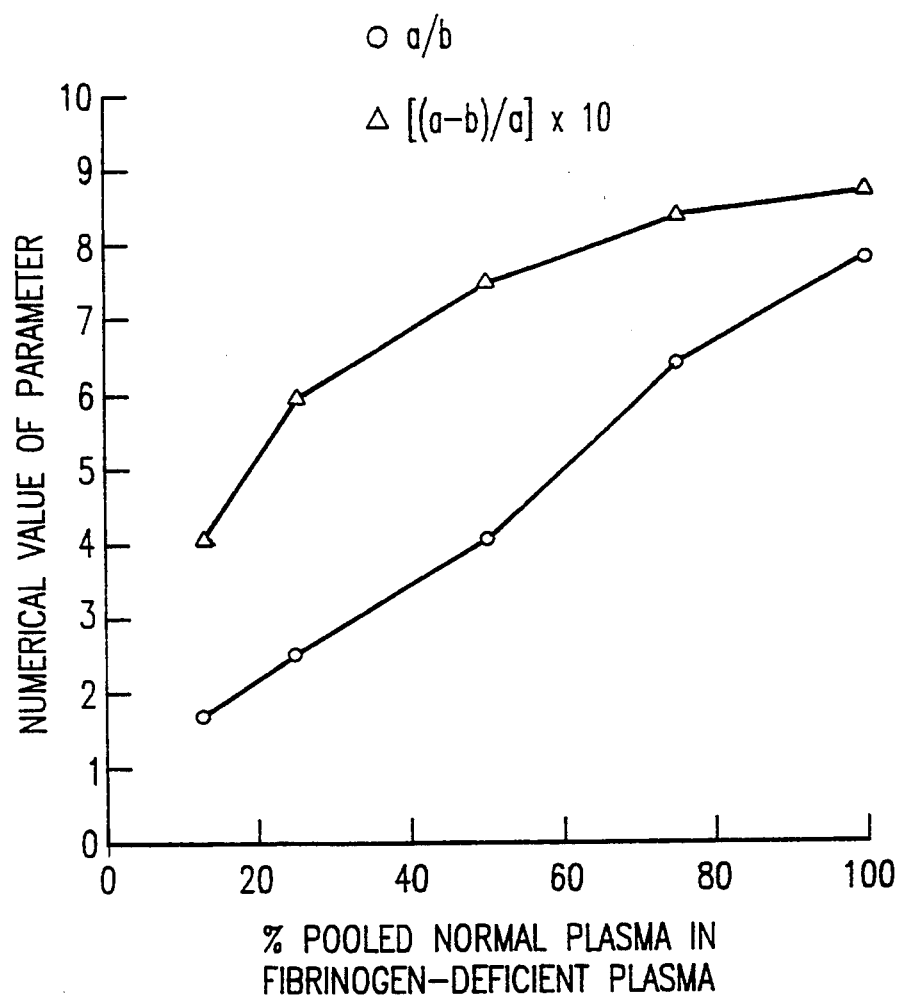

FIG. 6 shows the A/B and (A−B)/A curves on an expanded scale.

Figure 7:
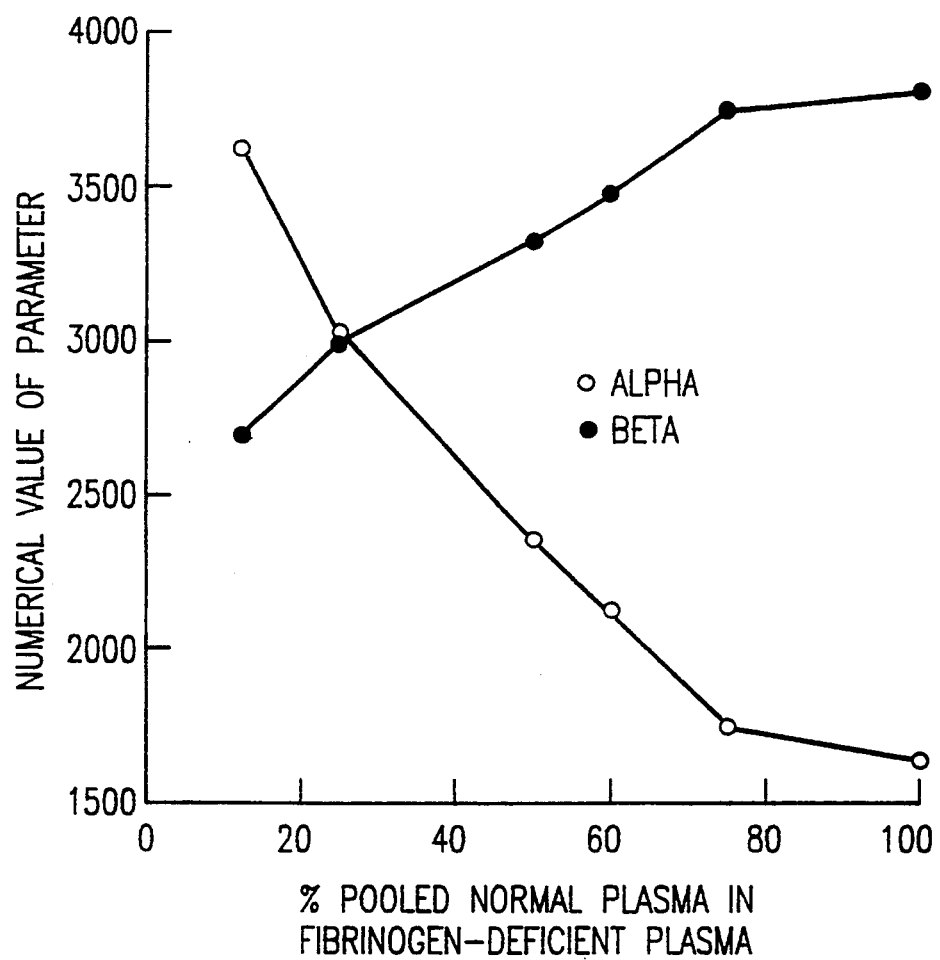

FIG. 7 shows $\alpha$ and $\beta$ values obtained in a different set of experiments. The $\alpha$ and $\beta$ values were obtained by integrating over the interval $t_{B'}$, where: $tB' = 90$ seconds.

Reptilase is generally preferred over thrombin for kinetic clotting based fibrinogen measurements because it is not affected by heparin, a commonly employed anticoagulant drug. In a preferred dry reagent formulation, reptilase (in buffer is combined with magnetic particles and polyethylene glycol of molecular weight (Mw) 3400 to 10,000. However, polyethylene glycol of molecular weights somewhat lower than 3400 and higher than 10,000 may be utilized. The dry reagent mix is prepared by dissolving the polyethylene glycol in water, and then adding the reptilase reagent and mixing gently. This solution is then mixed with magnetic particles and applied to reaction slides.

Another preferred dry reagent matrix is prepared from buffered reptilase, magnetic particles and bovine serum albumin. This is prepared by dissolving the bovine serum albumin in water, and then adding the reptilase reagent with gentle mixing. This solution is mixed with magnetic particles and applied to reaction slides.

It should be recognized that the first embodiment, which is based on clot formation kinetics, could typically utilize a lower concentration of clot forming reagent (thrombin or snake venom) than the second embodiment which is based on clotting time. The exact concentrations of reagents employed however, would vary with the type and source of the reagent (e.g., bovine, human, etc.) and potency as noted supra.

The first embodiment can also utilize thromboplastin as a clot forming reagent. Thromboplastin cannot be used as a clot forming reagent for the second end-point embodiment, because its use in this embodiment would not provide results specific for fibrinogen.

Yet another embodiment is to utilize a reagent concentration (of thrombin or snake venom) comparable to that in the first embodiment but to measure clotting time (as in the second embodiment) on an undiluted sample instead of clot kinetic parameters (as in the first embodiment). This approach provide a quantitative screening test which is sensitive over the most clinically useful range of fibrinogen levels (low normal to below normal) and can be useful in rapid assessment of fibrinogen abnormalities from an undiluted whole blood or plasma sample. Either thrombin or an appropriate snake venom (e.g., reptilase, copperhead venom or Malayan pit viper venom) may be utilized. This embodiment provides results analogous to a thrombin time, reptilase time, or equivalent test or a fibrinogen value when used with a standard curve for interpretation.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters Patent of the United States is

1. A method of performing a fibrinogen assay, comprising:
(i) subjecting to an oscillating magnetic field a reaction slide bearing (1) a sample well for receiving a liquid sample and (2) a reaction chamber containing a dry reagent matrix in which is embedded a plurality of magnetic particles distributed homogeneously therethrough, wherein said reagent is a protease which acts directly on fibrinogen and induces fibrin polymerization;

said sample well and reaction chamber being in fluid connection through a transport zone of geometry such that a volume of liquid analyte sample placed in said sample well and corresponding to the volume of said reaction chamber is transported from said sample well to said reaction chamber;

(ii) under conditions suitable for conducting a fibrinogen assay, adding a whole blood or a blood-derived sample to said sample well whereby said sample is introduced into said reaction chamber, said reagent is solubilized and said particles are freed to move in an oscillating pattern induced by said oscillating magnetic field, wherein said oscillating pattern has a start time and a stop time, corresponding to a change in the degree of particle movement relative to said oscillating magnetic field, said oscillating pattern rises in a kinetic particle oscillation curve to a peak maximum amplitude of particle oscillation, decreases to a post peak minimum amplitude of particle oscillation, and said kinetic particle oscillation curve has a measurable slope and area under the oscillation curve;

(iii) optically monitoring said reaction chamber to measure one or more of the following parameters (iiia) said start time and said stop time for said fibrinogen assay, or (iiib) the maximum amplitude of said particle oscillation, A, and the subsequent residual, post peak minimum amplitude, B, of said particle oscillation, or (iiic) the slope of said particle oscillation curve or area defined by said curve in the region between A and B; and (iv) using said start time and said stop time, or at least B, or said slope, or said area to correlate at least one of said parameters (iiia)–(iiic) to the concentration of clottable fibrinogen in standard samples to measure the concentration of clottable fibrinogen in said whole blood or blood-derived sample.

2. The method of claim 1, wherein said protease is one member selected from the group consisting of human thrombin, bovine thrombin, reptilase, copper head venom enzyme, or Malayan pit viper venom enzyme 3. A method of performing a clottable fibrinogen assay, comprising:

(i) subjecting to an oscillating magnetic field a reaction slide bearing (1) a sample well for receiving a liquid sample and (2) a reaction chamber containing a dry reagent matrix in which is embedded a plurality of magnetic particles distributed homogeneously therethrough, wherein said reagent is a fibrinogen assay reagent which acts directly on fibrinogen to induce fibrin polymerization;

said sample well and reaction chamber being in fluid connection through a transport zone of geometry such that a volume of liquid analyte sample placed in said sample well and corresponding to the volume of said reaction chamber is transported from said sample well to said reaction chamber;

(ii) under conditions suitable for conducting a fibrinogen assay, adding a whole blood or a blood-derived sample to said sample well whereby said sample is introduced into said reaction chamber, said reagent is solubilized and said particles are freed to move in an oscillating pattern induced by said oscillating magnetic field, wherein said oscillating pattern has a start time and a stop time, corresponding to a change in the degree of particle movement relative to said oscillating magnetic field, said oscillating pattern rises in a kinetic particle oscillation curve to a peak maximum amplitude of particle oscillation, decreases to a post peak minimum amplitude of particle oscillation, and said kinetic particle oscillation curve has a measurable slope and area under the oscillation curve;

(iii) optically monitoring said reaction chamber to measure said start time and said stop time for said fibrinogen assay; and (iv) using said start time and said stop time to correlate said start and stop time to the concentration of clottable fibrinogen in standard samples to measure the concentration of clottable fibrinogen in said whole blood or blood-derived sample.

4. The method of claim 3, wherein said dry reagent comprises thrombin.

5. The method of claim 3, wherein said dry reagent comprises reptilase, copperhead venom enzyme, or Malayan pit viper venom enzyme.

6. A method of performing a fibrinogen assay, comprising:

(i) subjecting to an oscillating magnetic field a reaction slide bearing (1) a sample well for receiving a liquid sample, (2) a reaction chamber, and (3) a conduit means situated between said sample well and said reaction chamber and being in fluid communication therewith;

said reaction chamber containing a dry reagent matrix in which is embedded a plurality of magnetic particles distributed homogeneously therethrough, wherein said dry reagent matrix is present only in said reaction chamber, and wherein said reagent is a fibrinogen assay reagent which acts directly on fibrinogen to induce fibrin polymerization;

(ii) under conditions suitable for conducting a fibrinogen assay, adding a volume of a whole blood or a blood-derived sample to said sample well, said volume of said sample being sufficient to substantially fill said conduit means without entering said reaction chamber or contacting said dry reagent matrix;

(iii) adding a volume of buffer diluent to said sample well, said volume of said buffer being sufficient to wash said sample into said reaction chamber thereby causing said reagent to become solubilized and freeing the particles to move in an oscillating pattern induced by said oscillating magnetic field, wherein said oscillating pattern has a start time and a stop time, corresponding to a change in the degree of particle movement relative to said oscillating magnetic field, said oscillating pattern rises in a kinetic particle oscillation curve to a peak maximum amplitude of particle oscillation, decreases to a post peak minimum amplitude of particle oscillation, and said kinetic particle oscillation curve has a measurable slope and area under the oscillation curve;

(iv) optically monitoring the oscillation of said magnetic particles to measure said start time and said stop time for the fibrinogen assay; and (v) using the start time and the stop time to correlate said start and stop time to the concentration of clottable fibrinogen in standard samples to measure the concentration of clottable fibrinogen in said whole blood or blood-derived sample.

7. A method of performing a clottable fibrinogen assay, comprising:
  (i) subjecting to an oscillating magnetic field a reaction slide bearing (1) a sample well for receiving a liquid sample and (2) a reaction chamber containing a dry reagent matrix in which is embedded a plurality of magnetic particles distributed homogeneously therethrough, wherein said reagent is a fibrinogen assay reagent which act directly on fibrinogen to induce fibrin polymerization;
  said sample well and reaction chamber being in fluid connection through a transport zone of geometry such that a volume of liquid analyte sample placed in said sample well and corresponding to the volume of said reaction chamber is transported from said sample well to said reaction chamber;
  (ii) under conditions suitable for conducting a fibrinogen assay, adding a whole blood or a blood-derived sample to said sample well whereby said sample is introduced into said reaction chamber, said reagent is solubilized and said particles are freed to move in an oscillating pattern induced by said oscillating magnetic field, wherein said oscillating pattern has a start time and a stop time, corresponding to a change in the degree of particle movement relative to said oscillating magnetic field, said oscillating pattern rises in a kinetic particle oscillation curve to a peak maximum amplitude of particle oscillation, decreases to a post peak minimum amplitude of particle oscillation, and said kinetic particle oscillation curve has a measurable slope and area under and area above the oscillation curve;
  (iii) optically monitoring said reaction chamber to measure the maximum amplitude of said particle oscillation, A, and the subsequent residual, post peak minimum amplitude, B, of said particle oscillation; and
  (iv) using at least B to correlate at least B to the concentration of clottable fibrinogen in standard samples to measure the concentration of clottable fibrinogen in said whole blood or blood-derived sample.

8. The method of claim 7, wherein only B is used to measure said fibrinogen concentration in said sample.

9. The method of claim 7, wherein a ratio A/B or B/A is used to measure said fibrinogen concentration in said sample.

10. The method of claim 7, wherein $A-B$ is used to measure said fibrinogen concentration in said sample.

11. The method of claim 7, wherein $(A-B) \div A$ or $A \div (A-B)$ is used to measure said fibrinogen concentration in said sample.

12. The method of claim 7, wherein A/B and $(A-B) \div A$ are used to measure said fibrinogen concentration of said sample.

13. The method of claim 7, wherein the slope of the oscillation curve taken at a region between A and B is used to determined fibrinogen concentration of said sample.

14. The method of claim 7, wherein the area either above or below the oscillation curve as defined by the region between A and B or a portion thereof is used to determine fibrinogen concentration of said sample.

15. The method of claim 7, wherein said dry reagent comprises thrombin.

16. The method of claim 7, wherein said dry reagent comprises reptilase, copperhead venom enzyme, or Malayan pit viper venom enzyme.

17. A method of performing a fibrinogen assay, comprising:
  (i) subjecting to an oscillating magnetic field a reaction slide bearing (1) a sample well for receiving a liquid sample, (2) a reaction chamber, and (3) a conduit means situated between said sample well and said reaction chamber and being in fluid communication therewith; said conduit means containing a dry reagent matrix in which is embedded a plurality of magnetic particles distributed homogeneously therethrough, wherein said dry reagent is present only in said conduit, and wherein said reagent is a fibrinogen assay reagent which acts directly on fibrinogen to induce fibrin polymerization;
  (ii) under conditions suitable for conducting a fibrinogen assay, adding a whole blood or blood-derived sample to said sample well, the volume of said sample being sufficient to substantially fill said conduit means and reaction chamber and to mix with said reagent and wash said reagent into said reaction chamber thereby freeing said magnetic particles to move in an oscillating pattern induced by said oscillating magnetic field, wherein said oscillating pattern has a start time and a Stop time, corresponding to a change in the degree of particle movement relative to said oscillating magnetic field, said oscillating pattern rises in a kinetic particle oscillation curve to a peak maximum amplitude of particle oscillation, decreases to a post peak minimum amplitude of particle oscillation, and said kinetic particle oscillation curve has a measurable slope and area under the oscillation curve;
  (iii) optically monitoring said reaction chamber to measure one or more of the following parameters (iiia) said start time and said stop time for said fibrinogen assay, or (iiib) the maximum amplitude of said particle oscillation, A, and the subsequent residual, post peak minimum amplitude, B, of said particle oscillation, or (iiic) the slope of said particle oscillation curve or area defined by said curve in the region between A and B; and
  (iv) using said start time and said stop time, or at least B, or said slope, or said area to correlate at least one of said parameters (iiia)–(iiic) to the concentration of clottable fibrinogen in standard samples to measure the concentration of clottable fibrinogen is said whole blood or blood-derived samples.

18. The method of claim 7, wherein, before step (ii), a volume of distilled water is added to said sample well, sufficient to be taken into said conduit via capillary action thereby solubilizing said dry reagent and freeing said magnetic particles prior to the addition of said whole blood or said blood-derived sample.

19. A method for performing a fibrinogen assay, comprising:
  (i) under conditions suitable for conducting a fibrinogen assay, adding a whole blood or blood-derived sample to a sample well of a reaction slide, said reaction slide bearing (1) said sample well for receiving a liquid sample, (2) a reaction chamber, and (3) a conduit means situated between said sample well and said reaction chamber and being in fluid communication therewith;
  said conduit means containing a dry reagent matrix in which is embedded a plurality of magnetic particles distributed homogeneously therethrough, wherein said dry reagent matrix is present only in said conduit, and wherein said reagent is a fibrinogen assay reagent which acts directly on fibrinogen to induce fibrin polymerization;

wherein the volume of said whole blood or said blood-derived sample added to said sample well is sufficient to substantially fill said conduit means and said reaction chamber and to wash said reagent into said reaction chamber thereby freeing said magnetic particles;

(ii) subjecting said reaction slide to an oscillating magnetic field either at the time of addition of said whole blood or said blood-derived sample to said sample well or shortly thereafter, wherein said oscillating magnetic field causes said freed magnetic particles to move in an oscillating pattern, wherein said oscillating pattern has a start time and a stop time, corresponding to a change in the degree of particle movement relative to said oscillating magnetic field, said oscillating pattern rises in a kinetic particle oscillation curve to a peak maximum amplitude of particle oscillation, decreases to a post peak minimum amplitude of particle oscillation, and said kinetic particle oscillation curve has a measurable slope and area under the oscillation curve; and (iii) optically monitoring said reaction chamber to measure one or more of the following parameters (iiia) at least the post peak minimum amplitude of said magnetic particle oscillation, (B), or (iiib) the slope of said particle oscillation curve, or (iiic) the area defined by the curve between the maximum amplitude of said particle oscillation, A, and B, to correlate at least one of said parameters (iiia)–(iiic) to the concentration of clottable fibrinogen in standard samples to measure the concentration of clottable fibrinogen in said whole blood or blood-derived sample.

* * * * *